United States Patent
Starzak (10) Patent No.: US 11,871,988 B1
(45) Date of Patent: Jan. 16, 2024

(54) MAPPING AND ENDOSCOPIC EXCISION OF A TUMOR USING INTRACAVITY LASER QUENCHING AND EMISSION SPECTROSCOPY

(71) Applicant: Michael E. Starzak, Washington, DC (US)

(72) Inventor: Michael E. Starzak, Washington, DC (US)

(*) Notice: Subject to any disclaimer, the term of this patent is extended or adjusted under 35 U.S.C. 154(b) by 0 days.

(21) Appl. No.: 18/060,745

(22) Filed: Dec. 1, 2022

(51) Int. Cl.
| | |
|---|---|
| *A61B 18/22* | (2006.01) |
| *A61B 5/00* | (2006.01) |
| *A61B 90/00* | (2016.01) |

(52) U.S. Cl.
CPC .......... *A61B 18/22* (2013.01); *A61B 5/0036* (2018.08); *A61B 5/0071* (2013.01); *A61B 5/0091* (2013.01); *A61B 2090/3614* (2016.02); *A61B 2090/373* (2016.02); *A61B 2090/3933* (2016.02); *A61B 2090/3941* (2016.02); *A61B 2218/007* (2013.01); *A61B 2562/0233* (2013.01)

(58) Field of Classification Search
None
See application file for complete search history.

(56) References Cited

U.S. PATENT DOCUMENTS

| | | | |
|---|---|---|---|
| 4,973,848 A | 11/1990 | Kolobanov et al. | |
| 5,699,798 A | 12/1997 | Hochman et al. | |
| 6,317,624 B1 | 11/2001 | Kollias et al. | |
| 6,387,350 B2 | 5/2002 | Goldenberg | |
| 8,139,911 B2 | 3/2012 | Konishi | |
| 10,842,566 B1 | 11/2020 | Hannaford et al. | |
| 10,986,997 B2 | 4/2021 | Bradbury et al. | |
| 2005/0000525 A1 | 1/2005 | Klimberg et al. | |
| 2007/0161854 A1 | 7/2007 | Alamaro et al. | |
| 2010/0189657 A1 | 7/2010 | Weissleder et al. | |

(Continued)

FOREIGN PATENT DOCUMENTS

WO WO2007070784 A2 6/2007

OTHER PUBLICATIONS

Starzak et al., Eu (III) Ion Binding to Poly (L-Glutamate) Anion Studied by Environment-Sensitive Laser Spectroscopy, Biopolymers, vol. 23, May 1984, DOI: https://doi.org/10.1002/bip.360230502, pp. 847-852.

(Continued)

*Primary Examiner* — Lynsey C Eiseman
*Assistant Examiner* — Amanda L Steinberg
(74) *Attorney, Agent, or Firm* — Schmeiser, Olsen & Watts, LLP (57) ABSTRACT

A device is provided for accurately mapping a tumor embedded in healthy tissue by using a probe ion that emits detectable light in response to the probe ion being bound to the tumor. An exciting laser beam is cleansed of light frequencies that excite the probe ion bound to the healthy tissue by using intracavity quenching that eliminates the wavelengths that excite the probe ion bound to the healthy tissue. A resulting emission from the probe ions bound to the tumor is photo-detected to illuminate the tumor and the periphery of the tumor. In one embodiment, the illumination of the tumor and its periphery is used to guide a surgical laser to accurately excise the tumor with a minimal loss of healthy tissue.

17 Claims, 4 Drawing Sheets

(56) References Cited

U.S. PATENT DOCUMENTS

2013/0066199 A1 3/2013 Ramanujan
2022/0346650 A1* 11/2022 Novak ................. A61B 5/0066

OTHER PUBLICATIONS

Lazarides et al., A Fluorescence-Guided Laser Ablation System for Removal of Residual Cancer in a Mouse Model of Soft Tissue Sarcoma, Theranostics, vol. 6, Issue 2, Jan. 1, 2016, pp. 155-166.
Yu-Cheng Chen, Optofluidic Biolasers in Tissues: Applications in Biology and Biomedicine, ORCID iD: 0000-0002-0008-5601, 2017, 152 pages.
Wang et al., Highly Sensitive Detection of Human Papillomavirus Type 16 DNA Using Time-Resolved Fluorescence Microscopy and Long Liftetime Probes, SPIE Proceedings vol. 2387, DOI: 10.1117/12.206816, published Apr. 12, 1995, pp. 162-168.
Doe, Human Genome Program, Contractor-Grantee Workshop IV, Nov. 13-17, 1994, Date published Oct. 1994, 274 pages.
Ogrinc et al., Cancer Surgery 2.0: Guidance by Real-Time Molecular Technologies, Trends in Molecular Medicine, CellPress, Jun. 2021, vol. 27, No. 6, DOI: http://doi.org/10.1016/j.molmed.2021.04.001, pp. 602-615.
Yu-Cheng Chen, et al., Lasing in blood, Optica, vol. 3, No. 8/Aug. 2016/ Optica, DOI: https://dx.doi.org/10.1364/OPTICA.3.000809, pp. 809-815.

* cited by examiner

MAPPING AND ENDOSCOPIC EXCISION OF A TUMOR USING INTRACAVITY LASER QUENCHING AND EMISSION SPECTROSCOPY

BACKGROUND

The present invention relates to biomedical instrumentation, and more particularly to a device for mapping and excising a tumor embedded in healthy tissue.

Medical imaging devices provide imaging of the interior of a body for clinical diagnosis and disease treatment. Imaging techniques, such as radiography, computed tomography, magnetic resonance imaging, positron emission tomography and single photon emission computed tomography, are used in preoperative tumor diagnosis, which has improved cancer patient care. The aforementioned imaging techniques, however, are not applicable or are not easily applied intraoperatively to tumor surgery. Intraoperative techniques for distinguishing between malignant and normal cells rely on palpation and visual inspection by the cancer surgeon. A more recent, known intraoperative approach uses a device for fluorescence image-guided surgery, which allows a surgeon to determine normal and malignant tissue in the operating field in real time through a detection of fluorescently labelled tissue (i.e., tissue injected with a fluorescent detection agent). Fluorescence image-guided surgery can be performed using endoscopes and other minimally invasive devices.

SUMMARY

In one embodiment, the present invention provides a first apparatus for mapping and excising a tumor embedded in non-tumorous biological tissue. The apparatus includes a dye laser system which includes a dye laser and a laser amplification cavity having an intracavity quenching chamber containing a mixture of sample non-tumorous biological tissue and probe ions. The probe ions in the mixture are of a single type of ion. Each of the probe ions has an absorption bandwidth that does not exceed a narrowness threshold bandwidth amount. The absorption wavelength peak of each of the probe ions shifts based on a local binding environment. The dye laser system is configured to emit a dye laser beam within a body of a living being. The sample non-tumorous biological tissue is initially in the body and in a proximity to a tumor in the body, and subsequently extracted from the body and placed in the dye laser system. The apparatus further includes an injection system for injecting a solution of probe ions in a concentration matching a concentration of the probe ions in the mixture contained in the intracavity quenching chamber. The injection system is configured to inject the solution in front of the dye laser beam emitted by the dye laser system to bind a first portion of the probe ions in the solution to a tumor in the body and bind a second portion of the probe ions in the solution to non-tumorous biological tissue in the body. The dye laser beam emitted from the dye laser system has wavelengths that excite the probe ions bound to the tumor to generate an emission of radiation, but do not excite the probe ions bound to the non-tumorous biological tissue in the body. The apparatus further includes a detector for detecting the emission of radiation generated by the probe ions bound to the tumor. The apparatus further includes a surgical cutting laser for generating a cutting beam. The surgical cutting laser is configured to cut tissue in a proximity to a boundary of the tumor by using the cutting beam. The boundary of the tumor is identified by the detected emission of radiation.

In another embodiment, the present invention provides a second apparatus for mapping boundaries of a tumor embedded in non-tumorous biological tissue and includes the dye laser system, injection system, and detector components of the first apparatus summarized above, but does not include the aforementioned surgical cutting laser.

In another embodiment, the present invention provides a method of mapping and excising a tumor embedded in non-tumorous biological tissue. The method includes generating, by a dye laser system, a dye laser beam by using an intracavity quenching technique applied to a mixture of sample non-tumorous biological tissue and probe ions so that the dye laser beam has wavelengths that excite probe ions bound to a tumor but do not excite probe ions bound to non-tumorous biological tissue. Each probe ion in the mixture has an absorption bandwidth that does not exceed a narrowness threshold bandwidth amount and has an absorption wavelength peak that shifts based on a local binding environment. The sample non-tumorous biological tissue is initially in a body of a living being and in a proximity to a tumor in the body and subsequently extracted from the body and placed in the dye laser system. The method includes emitting, by the dye laser system, the dye laser beam within the body. The method further includes injecting, by an injection system, a solution of probe ions in front of the dye laser beam to bind a first portion of the probe ions in the solution to the tumor in the body and a second portion of the probe ions in the solution to non-tumorous biological tissue in the body. The probe ions in the solution are in a concentration matching a concentration of the probe ions in the mixture to which the intracavity quenching technique is applied. The method further includes exciting, by the dye laser beam, the probe ions bound to the tumor, without exciting the probe ions bound to the non-tumorous biological tissue. The method further includes detecting, by a detector, an emission of radiation generated by the excitation of the probe ions bound to the tumor. The method further includes identifying, by the detector, boundaries of the tumor based on the detected emission of radiation. The method further includes cutting, by a surgical cutting laser, tissue in the body in a proximity to the identified boundaries of the tumor by using a cutting beam generated by the surgical cutting laser.

The aforementioned embodiments advantageously allow boundaries of a tumor to be measured accurately so that the tumor can be surgically removed, which results in a substantial reduction in an amount of non-tumorous biological tissue being removed along with the tumor as compared to known techniques for tumor excision.

DETAILED DESCRIPTION

Overview

Distinguishing between a tumor and healthy tissue during surgery is often difficult because of similarities in appearances and palpation results. Conventional intra-operative tumor margin assessment technologies have limitations, such as lacking real-time feedback, having limited sensitivity, and causing tissue damage. For example, known breast cancer resection techniques remove a volume of tissue significantly more than an optimal resection volume. Healthy tissue is also referred to herein as non-tumorous biological tissue. A tumor is also referred to herein as diseased tissue.

Embodiments of the present invention address the aforementioned unique challenges of mapping and excising a tumor embedded in non-tumorous biological tissue by using a probe ion that emits detectable light in response to the probe ion being bound to the tumor. An exciting laser beam is cleansed of light frequencies that excite the probe ions bound to the non-tumorous biological tissue. The aforementioned cleansing of light frequencies is done by using intracavity quenching that eliminates the wavelengths that excite the probe ion bound to healthy tissue. A resulting emission from the probe ions bound to the tumor is detected to illuminate the tumor and identify the boundaries of the tumor (i.e., boundaries between the tumor and non-tumorous biological tissue in which the tumor is embedded). In one embodiment, the illumination of the tumor and the identification of its boundaries is used to guide a surgical laser to accurately excise the tumor, resulting in minimal loss of healthy tissue near the boundaries of the tumor (i.e., substantially reduces the amount of healthy tissue that must be removed along with the tumor as compared to known tumor excision techniques). In one embodiment, the probe ion has a narrow excitation spectral bandwidth (i.e., the excitation spectral bandwidth is less than a predefined threshold amount), which is tuned to excite only the probe ion on binding sites that are spectrally unique to the probe ion on the tumor.

Apparatus for Mapping and Excising a Tumor

Figure 1:
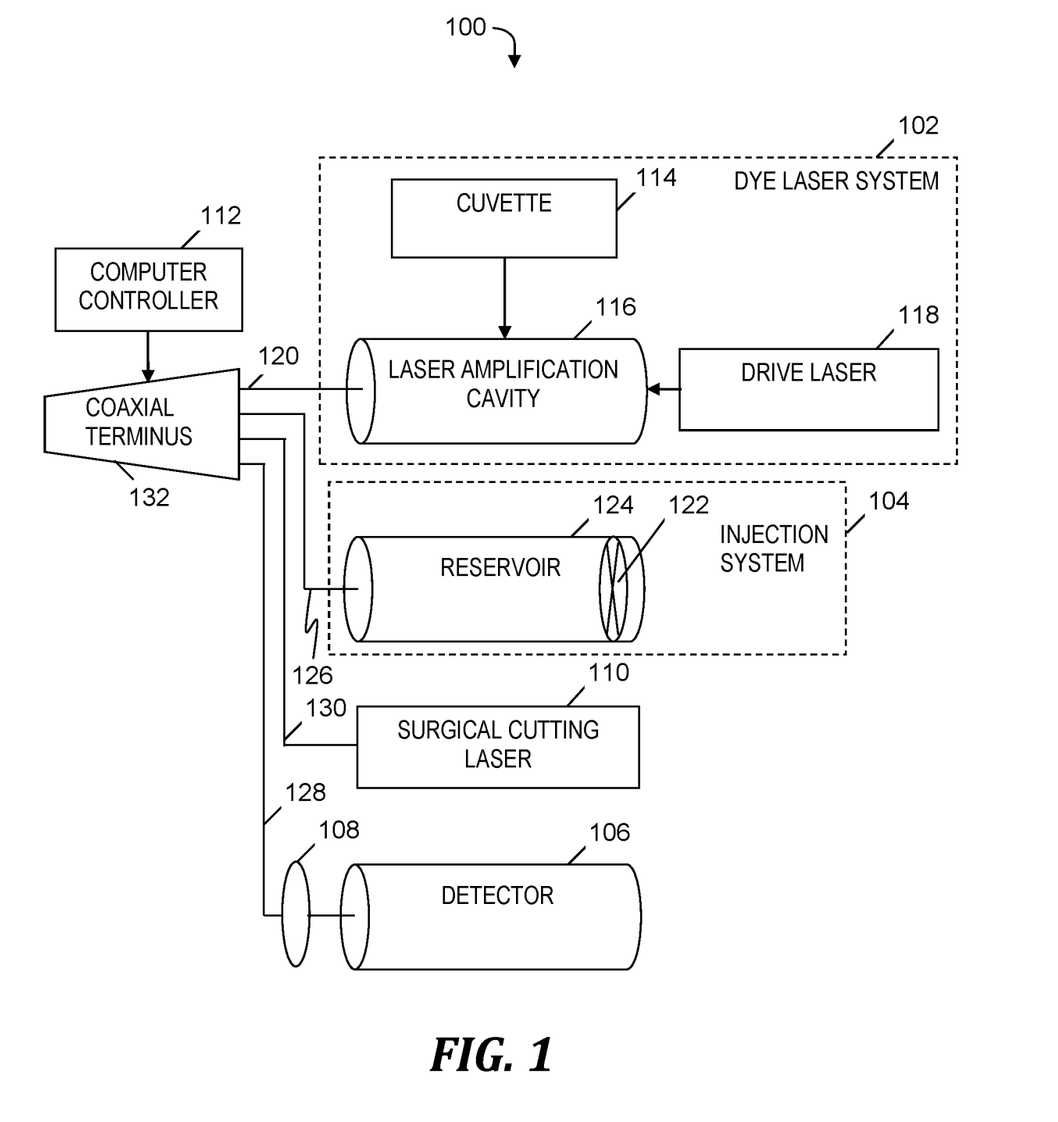
FIG. 1 is a block diagram of an apparatus for mapping and excising a tumor embedded in non-tumorous biological tissue, in accordance with embodiments of the present invention.

FIG. 1 is a block diagram of an apparatus 100 for mapping and excising a tumor embedded in non-tumorous biological tissue, in accordance with embodiments of the present invention. Apparatus 100 includes a dye laser system 102, an injection system 104, a detector 106, a filter 108, a surgical cutting laser 110, and a computer controller 112.

Dye laser system 102 includes a cuvette 114, a laser amplification cavity 116, and a drive laser 118. In one embodiment, cuvette 114 is a 100% non-reflective light transmitting cuvette containing a mixture of (i) probe ions (not shown) and (ii) a sample of non-tumorous biological tissue, which is placed in cuvette 114 after being extracted from its initial location in a region within a body of a living being. The probe ions in the mixture are of a single type of ion. As used herein, probe ions being of a single type of ion means that each of the probe ions of the single type of ion is the same chemical element with the same ionic charge. As used herein, "probe ions" in the plural means probe ions of a single type of ion.

The aforementioned region within the body includes a tumor being mapped and non-tumorous biological tissue in which the tumor is embedded. In one embodiment, the initial location of the sample of non-tumorous biological tissue in the body is in a proximity to the tumor in the body. In one embodiment, the region within the body is an organ or a portion of an internal organ in the body, where the internal organ is, for example, a pancreas, liver, kidney, lung, etc. In one embodiment, the initial location of the sample of non-tumorous biological tissue and the tumor being mapped are in the same internal organ in the body. In one embodiment, the sample of non-tumorous biological tissue being in a proximity to the tumor means that the non-tumorous biological tissue and the tumor are in the same internal organ in the body and the distance between the non-tumorous biological tissue and the tumor is less than a pre-defined distance.

Cuvette 114 having the probe ions (not shown) and the sample non-tumorous biological tissue is inserted into laser amplification cavity 116, which includes a fluorescing dye solution (not shown). After the insertion of cuvette 114 is inserted into laser amplification cavity 116, drive laser 118 excites laser amplification cavity 116 and an intracavity quenching technique is used to produce a laser light beam transmitted to the aforementioned region within the body via a first fiber optic cable 120. The laser light beam includes wavelengths that can be absorbed by probe ions bound to the tumor but cannot be absorbed by probe ions bound to the non-tumorous biological tissue in the aforementioned region. By using the aforementioned intracavity quenching technique, the laser light beam is transmitted through (i) all the probe ions bound on non-tumorous biological tissue, (ii) probe ions bound to sites equivalent on both healthy and tumorous tissue, and (iii) tumor sites that are environmentally unique. In one embodiment, only probe ions bound to sites on the tumor absorb orange light provided by the laser light beam and then re-emit 614 nm red light, which illuminates the tumor. The laser light beam produced by the excitation of the laser amplification cavity 116 is also referred to herein as a dye laser beam or simply as a laser beam or a beam. There is no mixing of the fluorescing dye solution in laser amplification cavity 116 and the contents of cuvette 114. Prior to inserting cuvette 114 into laser amplification cavity 116, an excitation by drive laser 118 of laser amplification cavity 116 having the fluorescing dye solution therein without the contents of cuvette 114 would emit a laser beam output at a range of wavelengths; e.g., 578 nm to 583 nm. After cuvette 114 is inserted into laser amplification cavity 116, the laser beam output has spectral gaps at the wavelengths in the aforementioned range of wavelengths (i.e., no radiation emitted at the wavelengths in the aforementioned range).

In one embodiment, the probe ions are trivalent europium (Eu(III)) ions and apparatus 100 takes advantage of the following properties of Eu(III) ions:

1. Eu(III) absorbs visible light in the visible region of the optical spectrum (i.e., orange light at a wavelength of 579.0 nanometers (nm)) and has a narrow absorption bandwidth in the visible region of the optical spectrum (i.e., the range of orange wavelengths absorbed). As used herein, a narrow bandwidth means that the bandwidth is less than a predefined narrowness threshold bandwidth amount. The narrowness of the absorption bandwidth for Eu(III) is a property of lanthanide ions in general.

2. The orange absorption at 579.0 nm for the Eu(III) ion in aqueous solution is extremely narrow (i.e., less than a predefined threshold amount).

3. The narrow absorption line in the 579 nm region is environment-sensitive, which means that that the absorption wavelength peak shifts for the Eu(III) ion in different local binding environments. For example, the absorption peak shifts if the Eu(III) ion is bound to a protein site.

4. The excited Eu(III) ion emits radiation in a visible region of the optical spectrum (i.e., emits red light at a wavelength of 614 nm), which can be detected using visible radiation detection instrumentation and can be detected exclusively with a proper filter 108 (i.e., detected with no excitation light, such as excitation light that does not strike an absorbing ion and is scattered back to detector 106).

5. The absorption at 579.0 nm for the Eu(III) ion is a 0-0 (i.e., single energy) transition for the $^0F$ to $^0D$ transition, which indicates that absorption for the Eu(III) ion occurs at a single peak wavelength for a specific site. By contrast, a second absorption region in the 464 nm region has multiple absorption lines for a specific ion site.

The "active" electrons combine together to form energy levels. The aforementioned terms D and F represent electron combinations having angular momentum proportional to two and three, respectively. The superscript zeroes in the aforementioned $^0F$ to $^0D$ transition indicate that each of the electron combinations has one energy level, so there is only one energy difference (i.e., one absorption line to jump between them). By contrast, the aforementioned second Eu(III) transition at about 464 nm has non-zero superscripts and there may be as many as five different absorption lines for a single ion binding site.

Injection system 104 includes a pump 122 that moves a solution of the probe ions from a reservoir 124 via a surgical tubing 126. In one embodiment, injection system 104 pumps aqueous Eu(III) ions directly in front of the exciting laser generated by dye laser system 102 as the tumor is being mapped by apparatus 100.

A second fiber optic cable 128 transmits light emitted by the probe ions bound to the tumor to detector 106 via filter 108. In one embodiment, detector 106 is a sensitive photodetector. Filter 108 is an interposed filter that removes extraneous and scattered light. In one embodiment, second fiber optic cable 128 picks up the radiation emitted from the Eu(III) ions bound to the tumor and transmits the radiation to detector 106 via filter 108, where detector 106 is configured for exclusively detecting radiation at a wavelength of 614 nm.

A surgical cutting laser beam generated by surgical cutting laser 110 is transmitted via a third fiber optic cable 130. In one embodiment, third fiber optic cable 130 brings a laser beam from a cutting ($CO_2$) laser to accurately cut tissue at the boundaries of the tumor and the healthy tissue. A laser beam is also referred to herein simply as a beam.

In one embodiment, apparatus 100 exploits the above-mentioned properties of Eu(III) ions by using emission spectroscopy (i.e., laser absorption-induced emission spectroscopy) by which a tunable dye laser having narrow spectral bandwidth scans through the spectral region in which the Eu(III) ion absorbs. When the laser wavelength from dye laser system 102 excites the Eu(III) probe ion, the resultant emission is detected by detector 106 to establish wavelengths of probe ion absorption in an absorption spectrum. In the 579 nm absorption region, there is one absorption peak for each type of ion binding site. For example, the Eu(III) ion binds only to identical sites on the helical form of poly-L-glutamate ion. In this example, a scan through the 579 nm spectral region reveals two spectrum lines for emissions: a first emission for the aqueous ion is observed at 579.0 nm and a second emission for the ion bound on the poly-L-glutamate sites at 579.15 nm. In this example, because aqueous Eu(III) is inserted into laser amplification cavity 116 using an intracavity quenching technique, the resultant laser emission from dye laser system 102 lacks the 579.0 wavelength for aqueous Eu(III), but still has the wavelengths to excite Eu(III) ions exclusively on the poly-L-glutamate sites.

In one embodiment, Eu(III) ions emit in the visible (i.e., red) spectral region at 614 nm, which is well-separated from the 579 nm excitation region, thereby allowing the emitted light to be selectively filtered and detected by filter 108 and detector 106.

Tumor tissue and non-tumorous biological tissue can have a number of distinct environments in which a probe ion such as Eu(III) can bind. Since the tumor and non-tumorous biological tissue are probably similar, many of the sites may be common to both types of tissue and may be closely spaced (i.e., spaced at a distance less than a predefined threshold distance). To be effective, apparatus 100 produces laser wavelengths only for probe ions bound on sites unique to the tumor tissue.

In one embodiment, dye laser system 102 provides laser intracavity quenching resulting from a mixture of the probe ions and a sample of non-tumorous biological tissue being inserted directly into laser amplification cavity 116 to spoil amplification of the excitation wavelength. Alternatively, a mixture of the probe ions and a material that mimics properties of the aforementioned sample of non-tumorous biological tissue is inserted into laser amplification cavity 116. The aforementioned material that mimics the properties may be healthy tissue extracted from another body that is different from the body in which the tumor being mapped is located. The laser amplification cavity 116 is configured so that photons are absorbed by an intracavity quenching chamber (not shown) included in laser amplification cavity 116 and are not amplified in the laser amplification cavity 116. That is, a laser beam resulting from dye laser system 102 using intracavity laser quenching lacks output radiation at wavelengths that excite the probe ions bound to the non-tumorous biological tissue but includes output radiation at wavelengths that excite the probe ions bound to the tumor. For example, aqueous Eu(III) in laser amplification cavity 116 eliminates the 579.0 laser emission to create a gap or hole in the output of dye laser system 102. A laser beam directed into a solution of aqueous Eu(III) ions lacks the wavelength to excite the aqueous Eu(III) ions. For example, a laser beam directed into an aqueous solution of Eu(III) ions and helical poly-L-glutamate anion results in only the Eu(III) ions on poly-L-glutamate absorbing light.

Diseased and healthy tissue from the same organ may have identical sites that cannot be used to distinguish the tissue. Intracavity quenching, however, provides a technique to target Eu(III) sites that exist only in diseased tissue. With a sample of healthy tissue in Eu(III) solution in the laser amplification cavity 116, the laser beam generated by dye laser system 102 amplifies and causes emissions from only the wavelengths for the Eu(III) probe ions on a site in the diseased tissue. With Eu(III) as the probe ion and dye laser system 102 optimized for the 579 nm spectral range, the excited probe ions on the diseased tissue glow red to allow for the imaging of the boundaries of the diseased tissue.

Using the aforementioned laser absorption-induced emission spectroscopy technique without the intracavity quenching technique to analyze a mixture of healthy and diseased tissue results in the number of distinct binding sites being significantly large, which makes a determination of possible absorptions exclusively for the diseased tissue difficult and time-consuming. Adding the aforementioned intracavity quenching technique facilitates a quicker determination of the possible absorptions exclusively for the diseased tissue.

The intracavity quenching technique includes placing a sample of material being studied in an intracavity quenching chamber included in the laser amplification cavity 116. Any wavelengths absorbed by the material cannot be amplified in the intracavity quenching chamber, so that the laser emission spectrum has gaps corresponding to the intracavity absorption.

For example, if a sample of Eu(III) and poly-L-glutamate are inserted into the laser amplification cavity 116, then the resultant laser beam lacks the wavelengths to excite either the Eu(III) or the poly-L glutamate in an external solution. If only aqueous Eu(III) is inserted into the laser amplification cavity 116, then the laser beam excites Eu(III) ions bound to the poly-L-glutamate. Much of the laser output in this example, however, is also channeled into wavelengths that are not absorbed by the probe ion on the protein and the intensity of the absorbing radiation is therefore reduced.

In one embodiment, a mixture of Eu(III) ions and healthy tissue from a biopsy are inserted into the intracavity quenching chamber included in the laser amplification cavity 116. The resultant laser beam lacks output radiation from wavelengths that excite Eu(III) ions bound to the healthy tissue. Such sites may also be present on diseased tissue, but if at least one site is different on the diseased tissue, or even slightly shifted, the light wavelengths exclusive to that site on the diseased tissue are amplified to excite exclusively the probe ion at the anomalous site. The excited probe ion subsequently emits radiation at 614 nm, by which it illuminates the tumor and its boundaries. First coaxial cable 120 transmits the resultant laser beam to the tumor and tissue surrounding the tumor in the body.

In one embodiment, surgical tubing 126 and first, second, and third fiber optic cables 120, 128, and 130 are included in a coaxial sleeve (i.e., coaxial cable) (not shown) that terminates at a coaxial terminus 132 (i.e., an active terminus). In other embodiments, surgical tubing 126 and first, second and third fiber optic cables 120, 128, and 130 are included in more than one coaxial sleeves, each having a coaxial terminus.

Computer controller 112 controls a movement of coaxial terminus 132 to the interface (i.e., boundaries or periphery) of the tumor and the non-tumorous biological tissue as determined by an emission of light by probe ions bound to the tumor caused by the beam from dye laser system 102 exciting the probe ions bound to the tumor. By controlling the movement of the coaxial terminus 132, computer controller 112 controls an emission of a laser beam by dye laser system 102, an injection of a solution of probe ions by injection system 104, and a cutting of tissue in proximity to the boundary of the tumor by surgical cutting laser 110.

In one embodiment, dye laser system 102 uses a laser dye having a natural radiation bandwidth of 5-10 nm to encompass the possible probe absorptions (e.g., 577 nm-583 nm), and which is transmitted to the coaxial terminus 132 via first fiber optic cable 120. In one embodiment, a power supply (not shown), pumps (not shown), and drive laser 118 included in dye laser system 102 are housed in an external master unit (not shown). In one embodiment, dye laser system 102 combines a biopsy sample of non-tumorous biological tissue and a saline solution that includes Eu(III) probe ions within the intracavity quenching chamber to produce radiation having wavelengths absorbable only by probe ions bound to a tumor in a target organ in the body of a human or other living being. The aforementioned biopsy sample is from the target organ.

In one embodiment, injection system 104 injects an Eu(III) solution directly in front of the laser beam generated by dye laser system 102 for binding and excitation by the laser beam. The binding by the laser beam includes binding a first portion of the Eu(III) ions in the injected solution to a tumor in a body of a living being and a second portion of the Eu(III) ions in the injected solution to healthy tissue in the body. The excitation by the laser beam includes exciting the Eu(III) ions bound to the tumor to generate an emission of radiation, without exciting the Eu(III) ions bound to the healthy tissue. The injected Eu(III) solution has a concentration of Eu(III) probe ions that matches the concentration of Eu(III) probe ions in the intracavity quenching chamber. The flow of the Eu(III) solution being injected is regulated by pump 122 (e.g., a peristaltic pump).

In one embodiment, second fiber optic cable 128 collects Eu(III) emission at 614 nm (i.e., at a red portion of the spectrum). In one embodiment, filter 108 is an interference filter (i.e., narrowband filter) that eliminates light scattering from the exciting laser beam radiation generated by dye laser system 102. In one embodiment, detector 106 is a red-sensitive photodetector that detects only the red emission. In one embodiment, computer controller 112 stores coordinates of radiation detected by detector 106, so that an additional coaxial probe can perform other operations on the tumor (e.g., packaging the tumor).

In one embodiment, surgical cutting laser 110 generates a laser beam and sends the laser beam to coaxial terminus 132 via third fiber optic cable 130 for cutting tissue in a proximity to a boundary of the tumor (i.e., at a configurable distance from a boundary of the tumor). The boundary of the tumor is identified by the emission of radiation generated by the probe ions bound to the tumor, where the emission is detected by detector 106. In one embodiment, light scattering from the laser beam generated by surgical cutting laser 110 is eliminated by filter 108 (e.g., an interference filter or a narrowband filter).

In one embodiment, the respective diameters of first, second, and third fiber optic cables 120, 128, 130 are small (i.e., between 0.5 and 2 millimeters (mm) for clad fiber optic cable) and the diameter of surgical tubing 126 is small (i.e., between 0.25 and 0.5 millimeters) to minimize the size of the coaxial sleeve and coaxial terminus 132, thereby easing the endoscopic insertion of the coaxial sleeve and terminus 132. In one embodiment, the first, second, and third fiber optic cables 120, 128, 130 and the surgical tubing 126 are each about 0.5 mm in diameter and the coaxial sleeve that includes first, second, and third fiber optic cables 120, 128, 130 and surgical tubing 126 is about 1 mm in cross-sectional diameter.

In one or more other embodiments, additional channels in the coaxial sleeve and terminus 132 include (i) a nozzle to inject sealant between the tumor tissue and the non-tumorous biological tissue to isolate the tumor in a package (i.e., encapsulate the tumor) immediately after an incision by surgical cutting laser 110, which allows for the removal of diseased cells when the tumor is removed endoscopically; (ii) a channel (i.e., aspiration tubing) to extract the sealed package containing the tumor via suction; and/or (iii) an aspirator to use suction to remove a substantial portion of the probe ion solution from the region of the excision of the tumor to minimize potential toxicity associated with the probe ions. Using suction to remove the substantial portion of the probe ion solution is performed subsequent to the boundary of the tumor being identified by the emission of radiation from probe ions bound to the tumor. In one embodiment in which the probe ions are Eu(III) probe ions, the aspirator to remove the probe ion solution from the excision region may be unnecessary because known medical instrumentation routinely uses other lanthanide ions (e.g., trivalent gadolinium ions (Gd(III)) for magnetic resonance imaging) without subsequent purging of the lanthanide ions. In one embodiment, the additional channels described in this paragraph are incorporated into a single coaxial sleeve along with the optical fiber cables and surgical tubing included in apparatus 100. In another embodiment, the additional channels describe in this paragraph are included in another coaxial sleeve whose terminus is directed by computer controller 112 to move to the stored coordinates of the location of boundaries of the tumor for encapsulation of the tumor, suction and removal of Eu(III) ions, and removal of the encapsulated tumor. The movement of the terminus of the other coaxial sleeve is performed by computer controller 112 subsequent to the movement of coaxial terminus 132 for emission of the laser beam by dye laser system 102, the injection of the solution of the probe ions by injection system 104, and the cutting of the tissue in the proximity of the boundary of the tumor by the surgical cutting laser 110.

In one embodiment, apparatus 100 includes a probe laser that is tunable to excite the probe ions exclusively on diseased or anomalous biological tissue.

Process for Mapping and Excising a Tumor

Figure 2:
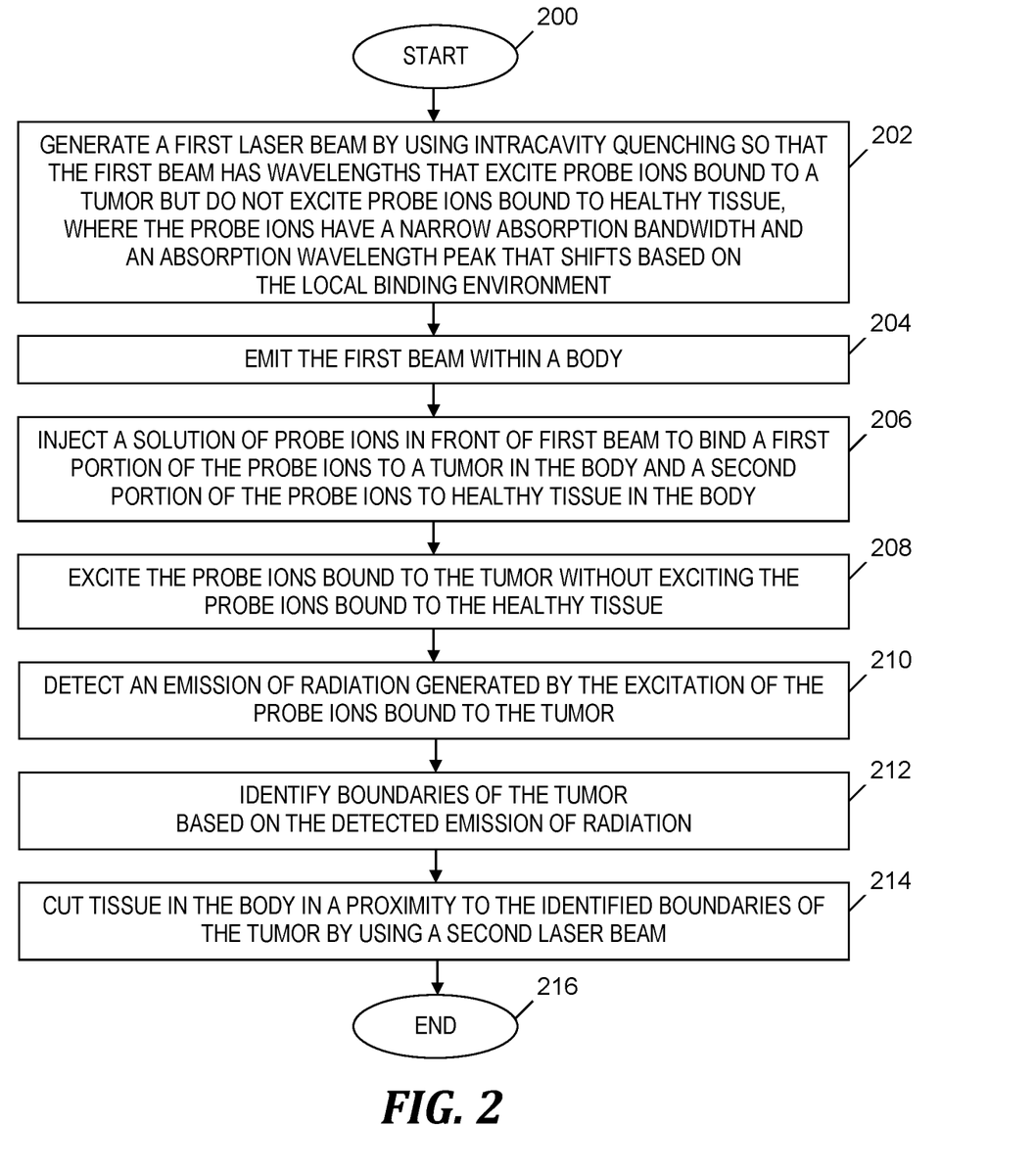
FIG. 2 is a flowchart of a process for mapping and excising a tumor embedded in non-tumorous biological tissue, in accordance with embodiments of the present invention.

FIG. 2 is a flowchart of a process for mapping and excising a tumor embedded in non-tumorous biological tissue, in accordance with embodiments of the present invention. The process of FIG. 2 begins at a start node 200. In step 202, dye laser system 102 (see FIG. 1) generates a first laser beam by using intracavity quenching so that the first laser beam has wavelengths that excite probe ions bound to a tumor but do not excite probe ions bound to non-tumorous biological tissue. The probe ions have a narrow absorption bandwidth and an absorption wavelength peak that shifts based on the local binding environment, as described above in the discussion of FIG. 1.

In step 204, dye laser system 102 emits the first laser beam within a body of a living being. Step 204 includes computer controller 112 (see FIG. 1) controlling a movement of coaxial terminus 132 to guide first optical fiber cable 120 to a target region in the body, where the target region includes a tumor and non-tumorous biological tissue in which the tumor is embedded. In one or more embodiments, the target region is an organ in the body or a portion of an organ in the body. In step 204, the first laser beam is emitted from first optical fiber cable 120.

In step 206, injection system 104 (see FIG. 1) injects a solution of probe ions in front of the first laser beam to bind (i) a first portion of the probe ions to the tumor in the target region and (ii) a second portion of the probe ions to the non-tumorous biological tissue in the target region.

In step 208, after the binding of the first and second portions of the probe ions, the first laser beam excites the probe ions bound to the tumor without exciting the probe ions bound to the non-tumorous biological tissue. The lack of excitation of the probe ions bound to the non-tumorous biological tissue is a result of the intracavity quenching in step 202 causing the first laser beam to lack wavelengths that excite probe ions bound to non-tumorous biological tissue. The excitation of the probe ions bound to the tumor generates an emission of radiation from the probe ions bound to the tumor.

In step 210, detector 106 (see FIG. 1) detects the emission of radiation generated by the excitation of the probe ions bound to the tumor and detects a lack of emission of radiation from the probe ions bound to the non-tumorous biological tissue in the target region.

In step 212, detector 106 (see FIG. 1) identifies boundaries of the tumor based on the detected emission of radiation from the probe ions bound to the tumor and the lack of emission of radiation detected for the probe ions bound to the non-tumorous biological tissue in the target region.

In step 214, surgical cutting laser 110 (see FIG. 1) cuts tissue in the target region in a proximity to the boundaries of the tumor identified in step 212. The cutting of tissue in step 214 is performed by a second laser beam, which is generated by surgical cutting laser 110 (see FIG. 1).

In one embodiment, computer controller 112 (see FIG. 1) controls one or more movements of coaxial terminus 132 (see FIG. 1) to place first optical fiber cable 120 (see FIG. 1), second optical fiber cable 128 (see FIG. 1), third optical fiber cable 130 (see FIG. 1), and surgical tubing 126 (see FIG. 1) to a proximity to the tumor and the non-tumorous biological tissue in the target region of the body to perform steps 204, 206, 208, 210, 212, and 214. First, second, and third optical fiber cables 120, 128, and 130 (see FIG. 1) and surgical tubing 126 (see FIG. 1) have respective ends located in coaxial terminus 132 (see FIG. 1). The generating of the first laser beam in step 202 includes dye laser system 102 (see FIG. 1) transmitting the first laser beam via first optical fiber cable 120 (see FIG. 1). The injecting of the solution in step 206 includes injection system 104 (see FIG. 1) transmitting the solution via surgical tubing 126 (see FIG. 1). The cutting of tissue in step 214 by using the second laser beam includes surgical cutting laser 110 (see FIG. 1) transmitting the second laser beam via third optical fiber cable 130 (see FIG. 1).

In one embodiment, the process of FIG. 2 further includes, subsequent to the tissue being cut in step 214: (1) a sealant channel (not shown in FIG. 1) encapsulating the tumor by placing a sealant between the tumor and the non-tumorous biological tissue at the boundaries identified in step 212; and (2) an aspiration channel (not shown in FIG. 1) removing the encapsulated tumor by suctioning the encapsulated tumor through an aspiration tubing (not shown in FIG. 1).

In one embodiment, the process of FIG. 2 further includes, subsequent to the tumor boundaries being identified in step 212, a suction port (not shown in FIG. 1)

removing the probe ions from the body by suctioning the probe ions via another tubing (not shown in FIG. 1).

EXAMPLE

Figure 3A:
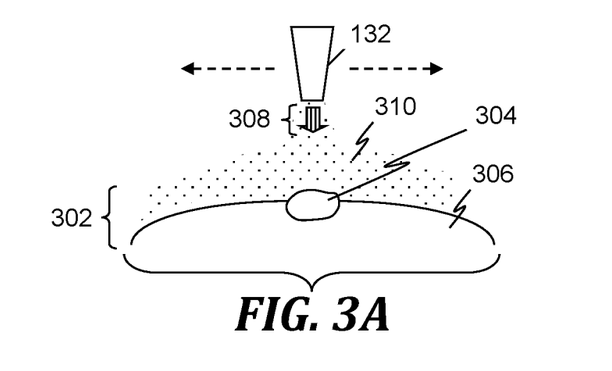
FIG. 3A depicts an example of steps performed in the process of FIG. 2, by which the apparatus of FIG. 1 emits a laser beam towards a target region of a body and injects a solution of probe ions in front of the laser beam, in accordance with embodiments of the present invention.

FIG. 3A depicts an example of steps 204 and 206 performed in the process of FIG. 2, by which apparatus 100 of FIG. 1 emits a laser beam 301 towards a target region 302 of a body and injects a solution of probe ions 303 in front of laser beam 301, in accordance with embodiments of the present invention. In an example of step 204 (see FIG. 2), dye laser system 102 (see FIG. 1) transmits laser beam 301 via a first optical fiber cable 120 (see FIG. 1), which has an end in coaxial terminus 132, which can be guided by computer controller 112 (see FIG. 1) to move relative to target region 302. Laser beam 301 is directed toward target region 302, which includes a tumor 304 and non-tumorous biological tissue 306. In an example of step 206 (see FIG. 2), injection system 104 (see FIG. 1) injects the solution of probe ions 303 in front of laser beam 301 to bind the probe ions 303 to tissue in target region 302.

Figure 3B:
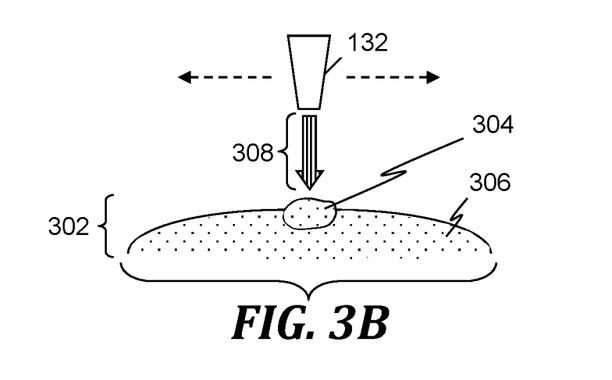
FIG. 3B depicts an example of a result of a step performed in the process of FIG. 2, by which a first portion of probe ions in the solution injected in the step depicted in FIG. 3A is bound to a tumor in target region 302 and a second portion of probe ions in the solution is bound to non-tumorous biological tissue in target region 302, in accordance with embodiments of the present invention.

FIG. 3B depicts an example of a result of step 206 performed in the process of FIG. 2, by which a first portion of probe ions in solution 303 (see FIG. 3A) injected in the step depicted in FIG. 3A is bound to a tumor 304 in target region 302 and a second portion of probe ions in the injected solution 303 (see FIG. 3A) is bound to non-tumorous biological tissue 306 in target region 302, in accordance with embodiments of the present invention. In an example of step 206 (see FIG. 2), injection system 104 (see FIG. 1) injects a solution of probe ions 303 (see FIG. 3A) in front of laser beam 308, via surgical tubing 126 (see FIG. 1), which has an end in coaxial terminus 132, which can move relative to target region 302. The injection of the solution of probe ions 303 (see FIG. 3A) in front of laser beam 308 results in a binding of a first portion of the probe ions to tumor 304, as indicated by the shaded portion of tumor 304, and a binding of a second portion of the probe ions to non-tumorous biological tissue 306, as indicated by the shaded portion of non-tumorous biological tissue 306. FIG. 3B also depicts an example of step 208 (see FIG. 2), by which laser beam 308 excites probe ions bound to tumor 304 without exciting the probe ions bound to non-tumorous biological tissue 306.

Figure 3C:
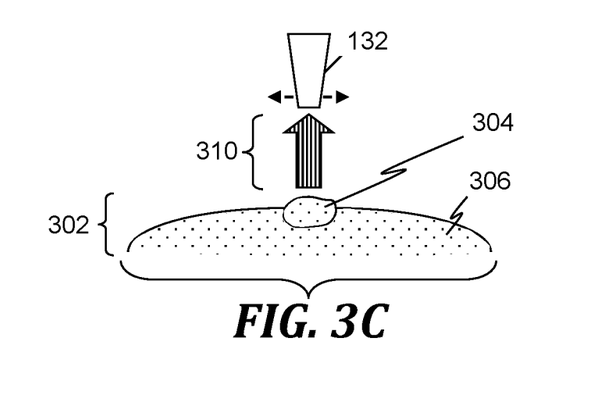
FIG. 3C depicts an example of a step performed in the process of FIG. 2, by which the apparatus of FIG. 1 detects an emission of radiation resulting from the step depicted in FIG. 3B, in accordance with embodiments of the present invention.

FIG. 3C depicts an example of step 210 performed in the process of FIG. 2, by which apparatus 100 of FIG. 1 detects an emission of radiation 310 resulting from the step depicted in FIG. 3B, in accordance with embodiments of the present invention. In an example of step 210 (see FIG. 2), detector 106 (see FIG. 1) uses second fiber optic cable 128 (see FIG. 1), which has an end in coaxial terminus 132, to detect an emission of radiation 310 from tumor 304, where the emission results from the excitation of the probe ions bound to tumor 304 without an excitation of the probe ions bound to non-tumorous biological tissue 306.

Figure 3D:
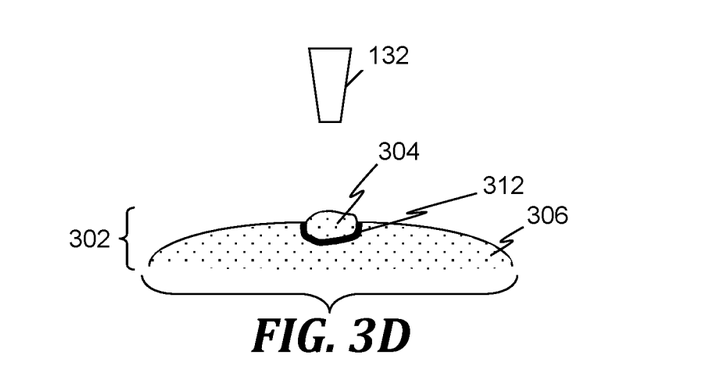
FIG. 3D depicts an example of a step performed in the process of FIG. 2, by which the apparatus of FIG. 1 identifies boundaries of a tumor based on a result of the step depicted in FIG. 3C, in accordance with embodiments of the present invention.

FIG. 3D depicts an example of step 212 performed in the process of FIG. 2, by which apparatus 100 of FIG. 1 identifies a boundary 312 of tumor 304 in target region 302 based on a result of step 210 depicted in FIG. 3C, in accordance with embodiments of the present invention. In an example of step 212, detector 106 (see FIG. 1) identifies boundary 312 between tumor 304 and non-tumorous biological tissue 306. The identification of boundary 312 is based on the emission of radiation 310 (see FIG. 3C) detected by detector 106 (see FIG. 1) via the second fiber optic cable 128 (see FIG. 1) which ends in coaxial terminus 132.

Figure 3E:
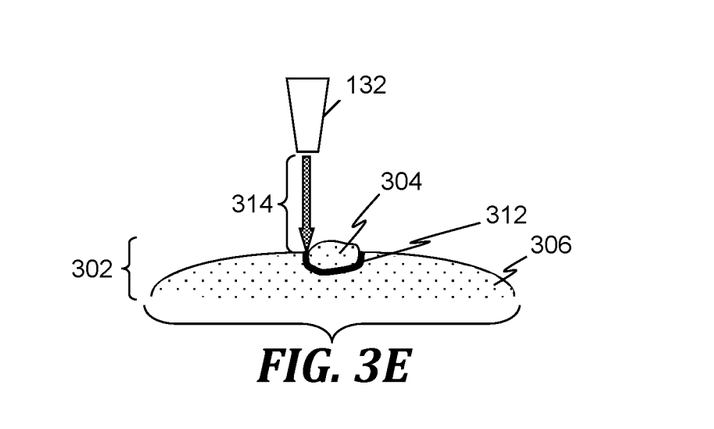
FIG. 3E depicts an example of a step performed in the process of FIG. 2, by which the apparatus of FIG. 1 cuts tissue in a proximity to a boundary of a tumor, where the boundary is identified in the step depicted in FIG. 3D.

FIG. 3E depicts an example of step 214 performed in the process of FIG. 2, by which apparatus 100 of FIG. 1 cuts tissue in a proximity to boundary 312 between tumor 304 and non-tumorous biological tissue 306 in target region 302, where boundary 312 is identified in step 212 (see FIG. 2) depicted in FIG. 3D. In an example of step 214 (see FIG. 2), surgical cutting laser 110 (see FIG. 1) emits second laser beam 314 via third optical fiber cable 130 (see FIG. 1), whose end is in coaxial terminus 132. Computer controller 112 (see FIG. 1) directs placement of coaxial terminus 132 and second laser beam 314 so that second laser beam 314 cuts tissue at the boundary 312 to remove tissue that includes tumor 304 with a minimal loss of healthy tissue as part of the removed tissue.

What is claimed is:

1. An apparatus for mapping and excising a tumor embedded in non-tumorous biological tissue comprising:
a dye laser system including a dye laser, a laser amplification cavity, and a mixture of sample non-tumorous biological tissue and probe ions being of a single type of ion, wherein each probe ion included in the probe ions has an absorption bandwidth that does not exceed a narrowness threshold bandwidth amount and whose absorption wavelength peak shifts based on a local binding environment, the dye laser system configured to emit a dye laser beam within a body of a living being, the sample non-tumorous biological tissue being initially in the body and in a proximity to a tumor in the body, and the sample non-tumorous biological tissue being extracted from the body and placed in the dye laser system;
an injection system for injecting a solution of probe ions in a concentration matching a concentration of the probe ions in the mixture included in the dye laser system, the injection system configured to inject the solution in front of the dye laser beam emitted by the dye laser system to bind a first portion of the probe ions in the solution to the tumor in the body and a second portion of the probe ions in the solution to non-tumorous biological tissue in the body, and the dye laser beam emitted from the dye laser system having wavelengths exciting the probe ions bound to the tumor to generate an emission of radiation, but not exciting the probe ions bound to the non-tumorous biological tissue in the body;
a detector for detecting the emission of radiation generated by the probe ions bound to the tumor; and
a surgical cutting laser for generating a cutting beam, the surgical cutting laser configured to cut tissue in a proximity to a boundary of the tumor by using the cutting beam, the boundary of the tumor being identified by the detected emission of radiation.

2. The apparatus of claim 1, wherein the laser amplification cavity is configured to use intracavity laser quenching so that wavelengths of radiation from the dye laser absorbed by the mixture are not amplified in the laser amplification cavity, and so that a laser beam resulting from the intracavity laser quenching lacks output radiation at wavelengths that excite the probe ions bound to the non-tumorous biological tissue in the body, but includes output radiation at wavelengths that excite the probe ions bound to the tumor.

3. The apparatus of claim 1, wherein the mixture of the sample non-tumorous biological tissue and the probe ions included in the dye laser system is included in an intracavity quenching chamber included in the laser amplification cavity.

4. The apparatus of claim 3, wherein the intracavity quenching chamber in the laser amplification cavity includes the probe ions and a material that mimics properties of the sample non-tumorous biological tissue.

5. The apparatus of claim 1, wherein the mixture of the sample non-tumorous biological tissue and the probe ions included in the dye laser system is in a cell that is external to the laser amplification cavity and in an optical path of a laser beam generated by the dye laser system.

6. The apparatus of claim 5, wherein the cell external to the laser amplification cavity includes the probe ions and a material that mimics properties of the sample non-tumorous biological tissue.

7. The apparatus of claim 1, wherein the probe ions in the mixture and the probe ions in the solution are trivalent europium (Eu(III)) ions having a 0-0 transition line at an absorption of 579 nanometers (nm), which provides an absorption by the Eu(III) ions at a single peak wavelength.

8. The apparatus of claim 1, further comprising:
a channel for introducing a sealant between the tumor and the non-tumorous biological tissue in the body to encapsulate the tumor; and
an aspiration tubing for a removal of the encapsulated tumor via suction.

9. The apparatus of claim 1, further comprising one or more coaxial cables, a terminus of the one or more coaxial cables, and a computer controller, wherein the dye laser system includes a first fiber optic cable for transmitting the dye laser beam, wherein the injection system includes a surgical tubing for injecting the solution in front of the dye laser beam, wherein the detector includes a second fiber optic cable that collects the emission of the radiation generated by the probe ions bound to the tumor, wherein the surgical cutting laser includes a third fiber optic cable for transmitting the cutting beam for cutting the tissue in the proximity to the boundary of the tumor, wherein the first, second, and third fiber optic cables and the surgical tubing are included in the one or more coaxial cables, and wherein the computer controller is configured to control a movement of the terminus of the one or more coaxial cables to a periphery of the tumor for controlling an emission of the dye laser beam by the dye laser system, an injection of the solution by the injection system, and a cutting of the tissue in the proximity of the boundary of the tumor by the surgical cutting laser.

10. The apparatus of claim 9, further comprising another coaxial cable, wherein the computer controller stores coordinates of a location of the tumor, and wherein the computer controller uses the stored coordinates of the location of the tumor to control a movement of the other coaxial cable to encapsulate and remove the tumor from the body, wherein the movement of the other coaxial cable is subsequent to the movement of the terminus of the one or more coaxial cables for controlling the emission of the dye laser beam by the dye laser system, the injection of the solution by the injection system, and the cutting of the tissue in the proximity of the boundary of the tumor by the surgical cutting laser.

11. The apparatus of claim 1, further comprising a suction port configured to remove the probe ions from the body subsequent to the boundary of the tumor being identified by the detected emission of radiation.

12. The apparatus of claim 1, further comprising a filter configured to eliminate light scattering from the dye laser beam emitted by the dye laser system and the cutting beam generated by the surgical cutting laser.

13. An apparatus for mapping boundaries of a tumor embedded in non-tumorous biological tissue comprising:

a dye laser system including a dye laser and a laser amplification cavity having an intracavity quenching chamber containing a mixture of sample non-tumorous biological tissue and probe ions being of a single type of ion, wherein each probe ion included in the probe ions has an absorption bandwidth that does not exceed a narrowness threshold bandwidth amount and whose absorption wavelength peak shifts based on a local binding environment, the dye laser system configured to emit a dye laser beam within a body of a living being, the sample non-tumorous biological tissue being initially in the body and in a proximity to a tumor in the body, and the sample non-tumorous biological tissue being extracted from the body and placed in the dye laser system;

an injection system for injecting a solution of probe ions in a concentration matching a concentration of the probe ions in the mixture contained in the intracavity quenching chamber, the injection system configured to inject the solution in front of the dye laser beam emitted by the dye laser system to bind a first portion of the probe ions in the solution to the tumor in the body and a second portion of the probe ions in the solution to non-tumorous biological tissue in the body, and the dye laser beam emitted from the dye laser system having wavelengths exciting the probe ions bound to the tumor to generate an emission of radiation, but not exciting the probe ions bound to the non-tumorous biological tissue in the body; and a detector for detecting the emission of radiation generated by the probe ions bound to the tumor for identifying boundaries of the tumor.

14. A method of mapping and excising a tumor embedded in non-tumorous biological tissue, comprising:

generating, by a dye laser system, a dye laser beam by using an intracavity quenching technique applied to a mixture of sample non-tumorous biological tissue and probe ions being of a single type of ion, so that the dye laser beam has wavelengths that excite probe ions bound to a tumor but do not excite probe ions bound to non-tumorous biological tissue, each probe ion in the mixture having an absorption bandwidth that does not exceed a narrowness threshold bandwidth amount and having an absorption wavelength peak that shifts based on a local binding environment, the sample non-tumorous biological tissue being initially in a body of a living being and in a proximity to a tumor in the body, and the sample non-tumorous biological tissue being extracted from the body and placed in the dye laser system;

emitting, by the dye laser system, the dye laser beam within the body;

injecting, by an injection system, a solution of probe ions in front of the dye laser beam to bind a first portion of the probe ions in the solution to the tumor in the body and a second portion of the probe ions in the solution to non-tumorous biological tissue in the body, the probe ions in the solution being in a concentration matching a concentration of the probe ions in the mixture to which the intracavity quenching technique is applied;

exciting, by the dye laser beam, the probe ions bound to the tumor, without exciting the probe ions bound to the non-tumorous biological tissue in the body;

detecting, by a detector, an emission of radiation generated by the excitation of the probe ions bound to the tumor;

identifying, by the detector, boundaries of the tumor based on the detected emission of radiation; and cutting, by a surgical cutting laser, tissue in the body in a proximity to the identified boundaries of the tumor by using a cutting beam generated by the surgical cutting laser.

15. The method of claim 14, further comprising:
controlling, by a computer controller, one or more movements of a coaxial terminus to place a first optical fiber cable, a second optical fiber cable, and a surgical tubing to a proximity to the tumor and the non-tumorous biological tissue in the body,
wherein the generating the dye laser beam includes transmitting the dye laser beam via the first optical fiber cable,
wherein the injecting the solution includes transmitting the solution via the surgical tubing,
wherein the cutting the tissue by using the cutting beam includes transmitting the cutting beam via the second optical cable, and
wherein the first and second optical fiber cables and the surgical tubing have respective ends at the coaxial terminus.

16. The method of claim 14, further comprising:
encapsulating, by a sealant channel, the tumor by placing a sealant between the tumor and the non-tumorous tissue in the body; and
removing, by an aspiration channel, the encapsulated tumor by suctioning the encapsulated tumor through an aspiration tubing.

17. The method of claim 14, further comprising removing, by a suction port, the probe ions from the body by suctioning the probe ions, wherein the removing is performed subsequent to the identifying the boundaries of the tumor.

* * * * *